(12) United States Patent
Metzger

(10) Patent No.: US 7,303,556 B2
(45) Date of Patent: Dec. 4, 2007

(54) DEVICE FOR SUPPLYING AN ELECTRO-PEN WITH ELECTRICAL ENERGY

(75) Inventor: Roger Metzger, Liestal (CH)

(73) Assignee: Synthes, Paoli, PA (US)

( * ) Notice: Subject to any disclaimer, the term of this patent is extended or adjusted under 35 U.S.C. 154(b) by 596 days.

(21) Appl. No.: 10/406,495

(22) Filed: Apr. 4, 2003

(65) Prior Publication Data

US 2003/0220638 A1 Nov. 27, 2003

Related U.S. Application Data

(63) Continuation of application No. PCT/CH00/00541, filed on Oct. 4, 2000.

(51) Int. Cl.
*A61B 18/14* (2006.01)
(52) U.S. Cl. .............................. 606/32; 606/34; 606/41
(58) Field of Classification Search .................. 606/32, 606/34, 41; 607/101, 103, 145, 146, 149–151
See application file for complete search history.

(56) References Cited

U.S. PATENT DOCUMENTS

| | | | | |
|---|---|---|---|---|
| 4,593,691 A | * | 6/1986 | Lindstrom et al. ............. | 606/45 |
| 5,413,590 A | | 5/1995 | Williamson .................. | 607/75 |
| 5,561,881 A | * | 10/1996 | Klinger et al. ................ | 15/22.1 |
| 6,086,585 A | | 7/2000 | Hovda et al. .................. | 606/45 |
| 6,120,496 A | | 9/2000 | Whayne et al. ................ | 606/1 |
| 6,241,723 B1 | * | 6/2001 | Heim et al. ................... | 606/34 |
| 6,533,778 B2 | * | 3/2003 | Herzon ........................ | 606/28 |
| 6,558,382 B2 | * | 5/2003 | Jahns et al. .................... | 606/41 |
| 6,666,875 B1 | * | 12/2003 | Sakurai et al. .............. | 606/169 |
| 2002/0006275 A1 | * | 1/2002 | Pollack ........................ | 392/380 |

FOREIGN PATENT DOCUMENTS

| | | |
|---|---|---|
| DE | 197 13 224 A1 | 10/1998 |
| GB | 2 128 093 A | 4/1984 |
| WO | WO9806144 * | 2/1998 |

* cited by examiner

*Primary Examiner*—Lee S. Cohen
(74) *Attorney, Agent, or Firm*—Jones Day

(57) ABSTRACT

The invention relates to a device for supplying electrical energy to an electro-pen with an electric drive unit for driving a tool. The device comprises a console with an energy supply unit having an accumulator for supplying the electrical drive unit with electrical energy. The console may be configure to be sterilized by steam having a housing and electrical components that are sealed liquid-tight. The accumulator may include a sterile covering for sterile introduction into the console. A coupling between the console and the electro-pen carries the supply of electrical energy from the console to the electro-pen. The coupling may be an electrical contact in the form of a sterilizable connector or an inductive coupling. The console may be configured to store energy and is thus mobile, or the console may include a connection for connecting to a mains or external power supply for charging the accumulator. The console may include a switch-mode power supply for charging the accumulator. The console may include a holder for receiving and charging the electro-pen. The electro-pen includes an electrical storage device and a coupling for receiving the electrical energy supply from the accumulator. The holder may include an electrical coupling between the console and the electro-pen in which at least two electrical contacts and at least one transformer are disposed about each the holder and the electro-pen. Alternatively, the holder may include an inductive coupling in which at least one transformer having at least one coil is disposed about each the holder and the electro-pen.

20 Claims, 1 Drawing Sheet

US 7,303,556 B2

DEVICE FOR SUPPLYING AN ELECTRO-PEN WITH ELECTRICAL ENERGY

CROSS-REFERENCE TO RELATED APPLICATIONS

The application is a continuation of the U.S. National Stage designation of copending International Patent Application PCT/CH00/00541, filed Oct. 4, 2000, the entire content of which is expressly incorporated herein by reference thereto.

FIELD OF THE INVENTION

The invention relates to a device for supplying an electro-pen with electrical energy.

BACKGROUND OF THE INVENTION

Devices known in the art which supply electrical energy to an electro-pen are often applied in the medical field, in particular, surgical procedures. Electro-pens are typically used, for example, in operations in the visual and hand area.

Electro-pens, according to the state of the art, consist of a drive unit in the form of a pen, i.e., in the form of a pen holder, an electric cable, and a console which converts the mains voltage into a low voltage suitable for the drive unit.

An electromagnetic pen for the treatment of humans and animals is disclosed in German Patent Application No. DE 19713224 A1. The electro-pen serves, with the aid of low intensity magnetic fields, to introduce drugs through the skin of humans and animals without perforating the skin. This electro-pen is operated with two microbatteries connected in tandem. Electro-pens known according to the aforementioned state of the art have the disadvantage that the energy supplying console with energy supply unit cannot be sterilized due to its construction. Furthermore, the console, as a rule, is plugged into a socket outlet and is therefore immobile.

SUMMARY OF THE INVENTION

The present invention is directed to a device for supplying electrical energy to an electro-pen comprising a console with an energy supply unit having an accumulator for supplying the electrical drive unit with electrical energy, and a coupling, operably associated with and between the console and the electro-pen, for carrying the supply of electrical energy from the console to the electro-pen. In addition, the console is configured to be sterilized by steam.

In one embodiment, the coupling is an electrical coupling. The electrical coupling may be a sterilizable cable connector. In another embodiment, the coupling is an inductive coupling. The inductive coupling includes at least one transformer having at least one coil disposed on the console operably associated with at least one transformer having at least one coil disposed on the electro-pen.

The device also may include a housing for enclosing the console. The housing is sealed liquid-tight. In addition to the housing, the device may further comprise electrical components that are also sealed liquid-tight.

In a preferred embodiment, the console is configured to store energy and is thus mobile. Alternatively in another embodiment, the console may include a connection for connecting to a mains or external power supply for charging the accumulator.

In another embodiment, the console includes a holder for receiving the electro-pen. The holder includes an electrical coupling between the console and the electro-pen for carrying the supply of electrical energy from the console to the electro-pen. The electrical coupling includes at least two electrical contacts and at least one transformer disposed about the holder operably associated with at least two electrical contacts with at least one transformer disposed on the electro-pen. In another embodiment, the holder includes, alternatively, an inductive coupling. The inductive coupling includes at least one transformer having at least one coil operably disposed about the holder operably associated with at least one transformer having at least one coil disposed on the electro-pen.

In another embodiment, the device may further comprise a sterile covering disposed about the accumulator for sterilely introducing the accumulator into the console. Also, the device may include a switched-mode power supply for charging the accumulator.

In a preferred embodiment, an electro-pen for use with the energy supplying device as described above, comprising an electrical energy storage device for receiving and storing the electrical energy from the accumulator. The energy storage device is configured with an electrical coupling for receiving an electrical supply from the accumulator. Alternatively, the energy storage device is configured with an inductive coupling for receiving an electrical supply from the accumulator.

In another embodiment, a chargeable driver system comprises an electro-pen having a drive unit for actuating a tool, a console with an energy supply unit, in which the console defines a chamber for receiving the electro-pen and is sealed liquid-tight for sterilization. In addition, the console further includes an accumulator for storing electrical energy, and a coupling is operably associated with and between the console and the electro-pen for supplying the electro-pen with electrical energy. The electro-pen of the chargeable driver system may have an electrical energy storage device operably associated with the coupling for receiving and storing the electrical energy from the accumulator. In one embodiment, the coupling is configured for electrical coupling. Alternatively the coupling may be configured for inductive coupling.

As previously described, the console is configured to be liquid-tight in order to ensure that it can be sterilized and is resistant to hot steam. Steam sterilization occurs at a temperature of 143° C., a relative humidity of 100%, and a pressure of 3 bar.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
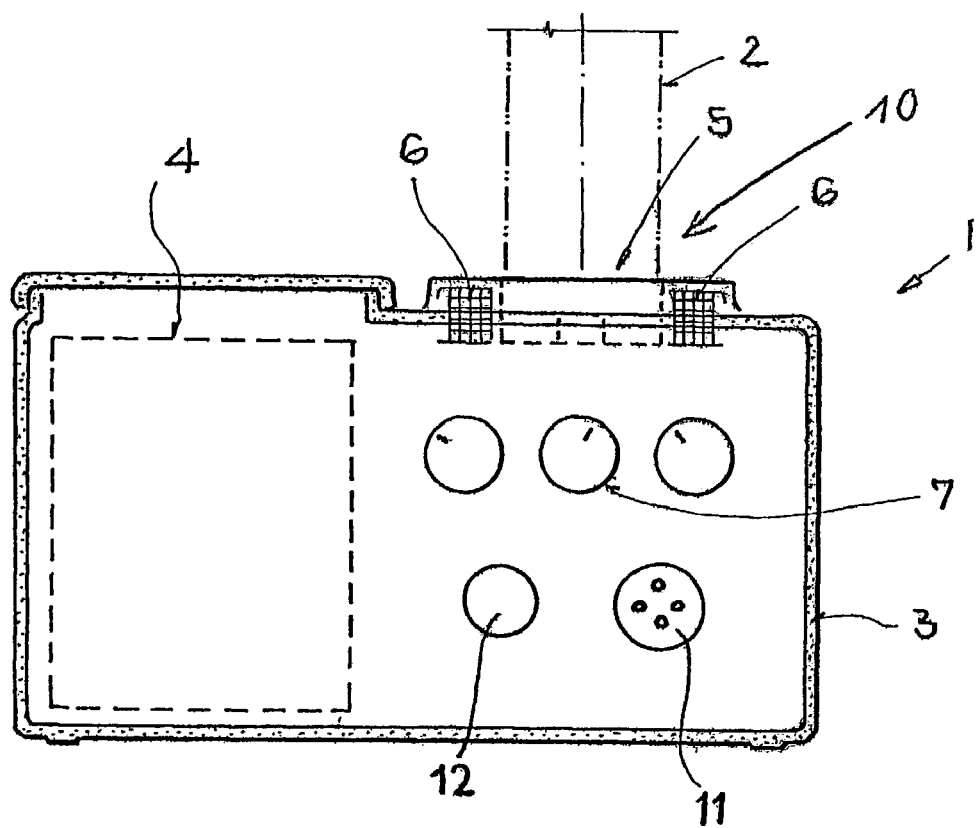
FIG. 1 shows one embodiment of the device according to the present invention with a console and energy supply unit as well as an electro-pen.
Figure 1:
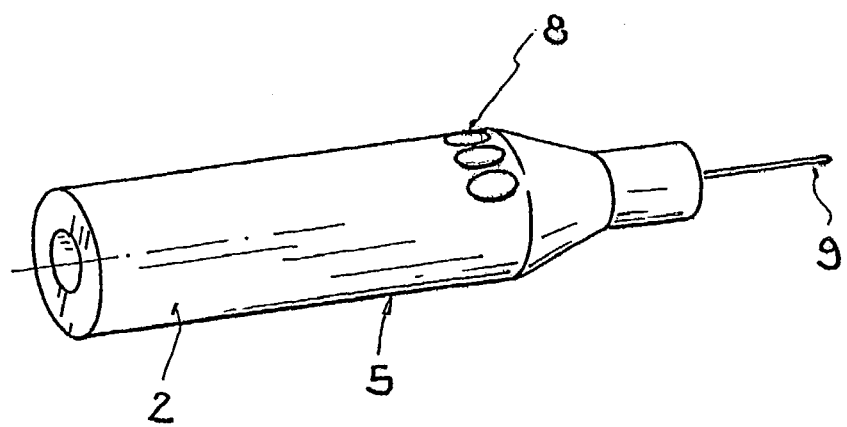

For convenience, the same or equivalent elements in various embodiments of the invention illustrated in the drawings have been identified with the same reference numerals. Further, in the description that follows, any reference to either orientation or direction is intended primarily for the convenience of description and is not intended in any way to limit the scope of the present invention thereto.

FIG. 1 shows a preferred embodiment of the electrical energy supplying device according to the present invention. The device for supplying an electro-pen with electrical energy comprises a console with an energy supply unit 1 having operating elements 7 as well as an electro-pen 2 having operating elements 8. The electro-pen 2 is supplied with electrical energy either directly via an electrical cable or indirectly via induction through electrical contacts and a small energy storage device, which will be discussed in greater detail below. The electro-pen 2 is equipped with an electrical drive unit 5 for driving a tool. Typically the drive unit 5 of electro-pen 2 is an electric motor, although other drive units are also contemplated which are moved through translation instead of through rotation.

The console 1 is enclosed in a liquid-tight housing 3, and is thus configured for sterilization. Steam sterilization may generally occur at a temperature of 143° C., a relative humidity of 100%, and a pressure of 3 bar. Because the console 1 may be sterilized, it may be operated directly by the surgeon performing the surgical procedure, unlike traditional console and energy supply units. In addition, the console 1 is capable of operation independent of the mains or external power supply, and thus, the console 1 is mobile. To facilitate independent operation, the console 1 is equipped with an accumulator or rechargeable battery 4 as energy source. The accumulator 4 may have a sterile covering for sterile introduction of the accumulator 4 into the console 1.

In one embodiment, a small, rapidly chargeable electrical energy source (for example, a capacitor) is housed in the electro-pen 2 which can be charged via the accumulator 4 through an electrical or inductive coupling with a corresponding device on the console 1. This configuration has the advantage in that it avoids requiring a large and heavy accumulator in the electro-pen 2. The console 1 has a receiving holder or chamber 10 in which the electro-pen 2 may be received for charging. In an embodiment having an inductive coupling, one or more transformer 6 having at least one coil is located in the console 1. In one exemplary embodiment, transformer 6 may be disposed about the holder 10. This transformer 6 is used in connection with another one or more transformers having at least one coil located in the electro-pen 2 to charge the electro-pen 2. In an alternate embodiment having electrical coupling, at least two electrical contacts having one or more transformer 6 are provided in the console 1, and transformer 6 may be disposed about the holder 10. The electrical contacts of the console 1 work in conjunction with another at least two electrical contacts having one or more transformers disposed in the electro-pen 2 in order to charge the electro-pen 2.

In another embodiment, the console 1 may have an electrical cable connection 12 for operating and electrically supplying the electro-pen 2. In addition, the cable may be capable of being sterilized. Also, the console 1 may also still be provided with a connection 11 for connecting to the mains or external power supply in order to charge the accumulator 4. Additionally, the console 1 may include a switch-mode power supply for supplying the charge to the accumulator 4.

One will appreciate that the electrical energy supplying device is mobile and therefore advantageously does not require a physical connection to a mains or an external power supply during use. In addition, the device possesses a console, which is portable and capable of being sterilized. Since the device is configured to supply the electrical energy to the electro-pen, the omission of a battery in the electro-pen makes the electro-pen significantly lighter than conventional battery operated electro-pens and is thus easier to handle. In addition, any connection of the electro-pen to an unsterile area may be avoided. Because the console and energy supply unit may be sterilized, all the functions of the device and electro-pen can be operated directly by the surgeon performing the surgical procedure, unlike conventional console and energy supply units. In one embodiment, in which the electro-pen is used with the device of the present invention, an advantage exists where the electrical supply cable is omitted and integration of a large and heavy accumulator into the electro-pen may be avoided.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed is:

1. A device for supplying electrical energy, comprising:
   an electro-pen having an electrical drive unit for driving a tool;
   a console with an energy supply unit having an accumulator for storing and supplying the electrical drive unit with electrical energy; and
   a coupling operably associated with and between the console and the electro-pen for carrying electrical energy from the console to the electro-pen,
   wherein the console is sealed liquid-tight for sterilization by steam, and
   wherein the electro-pen includes an electrical energy storage device for receiving and storing the electrical energy from the accumulator of the device.

2. The device of claim 1, wherein the coupling is a direct electrical connection having a sterilizable cable connector.

3. The device of claim 1, wherein the coupling is an inductive coupling.

4. The device of claim 3, wherein the inductive coupling includes at least one transformer having at least one coil disposed on the console operably associated with the electro-pen.

5. The device of claim 1, further including a housing for enclosing the console, wherein the housing is sealed liquid-tight.

6. The device of claim 1, wherein electrical components of the console are sealed liquid-tight.

7. The device of claim 1, wherein the console is configured to store energy and is thus mobile.

8. The device of claim 1, wherein the console includes a connection for connecting to an external power supply for charging the accumulator.

9. The device of claim 1, wherein the console includes a holder for receiving the electro-pen, the holder includes an electrical coupling between the console and the electro-pen for carrying electrical energy from the console to the electro-pen.

10. The device of claim 1, wherein the console includes a holder for receiving the electro-pen, the holder includes an inductive coupling between the console and the electro-pen for carrying electrical energy from the console to the electro-pen.

11. The device of claim 10, wherein the inductive coupling includes at least one transformer disposed about the holder having at least one coil operably associated with the electro-pen for charging the electrical drive unit of the electro-pen.

12. The device of claim 1, wherein a sterile covering is disposed about the accumulator for sterilely introducing the accumulator into the console.

13. The device of the claim 1, further including a switched-mode power supply for charging the accumulator.

14. The device of claim 1, wherein the energy storage device is configured with an electrical coupling for receiving an electrical supply from the accumulator.

15. The device of claim 1, wherein the energy storage device is configured with an inductive coupling for receiving an electrical supply from the accumulator.

16. A chargeable driver system comprising:
   an electro-pen having a drive unit for actuating a tool;
   a console with an energy supply unit, the console defining a chamber for receiving the electro-pen, the console further including an accumulator for storing electrical energy; and
   a coupling operably associated with and between the console and the electro-pen for supplying the electro-pen with electrical energy;
   wherein the console is sealed liquid-tight for sterilization, and
   wherein the electro-pen includes an electrical energy storage device for receiving and storing the electrical energy from the accumulator of the device.

17. The chargeable driver system of claim 16, wherein the system further includes a connector operably associated with the accumulator for selectively connecting to an external power supply and receiving an electrical charge.

18. The chargeable driver system of claim 16, wherein the coupling is a sterilizable electrical cable connector.

19. The chargeable driver system of claim 16, wherein the coupling is an inductive coupling and includes at least one transformer having at least one coil disposed on the console operably associated with the electro-pen.

20. A chargeable driver system comprising:
   an electro-pen having a drive unit for actuating a tool;
   a console with an energy supply unit, the console defining a chamber for receiving the electro-pen, the console further including an accumulator for storing electrical energy, the console being sealed liquid-tight for sterilization; and
   a coupling operably associated with the console for supplying the electro-pen with electrical energy,
   wherein the electro-pen has an electrical energy storage device operably associated with the coupling for receiving and storing the electrical energy from the accumulator.

* * * * *